United States Patent [19]

Collington et al.

[11] Patent Number: 4,855,293

[45] Date of Patent: Aug. 8, 1989

[54] ANTI-INFLAMMATORY COMPOSITIONS COMPRISING A SYSTEMIC NON-STEROIDAL ANTI-INFLAMMATORY DRUG AND A CYCLOPENTYL ETHER

[75] Inventors: Eric W. Collington, Knebworth; Harry Finch, Letchworth; Duncan B. Judd, Ware, all of England

[73] Assignee: Glaxo Group Limited, London, England

[21] Appl. No.: 111,026

[22] Filed: Oct. 21, 1987

[30] Foreign Application Priority Data

Oct. 22, 1986 [GB] United Kingdom ................ 8625325

[51] Int. Cl.[4] .................. C07C 177/00; A61K 31/557; A61K 31/55
[52] U.S. Cl. .................................... 514/212; 514/613; 514/708; 514/165
[58] Field of Search ................ 514/212, 613, 708, 165

[56] References Cited

FOREIGN PATENT DOCUMENTS

| | | |
|---|---|---|
| 0178121 | 4/1986 | European Pat. Off. . |
| 1486832 | 9/1977 | United Kingdom . |
| 2101483 | 1/1983 | United Kingdom . |
| 2120938 | 12/1983 | United Kingdom . |
| 2148710 | 6/1985 | United Kingdom . |
| 2174702 | 11/1986 | United Kingdom . |

OTHER PUBLICATIONS

Collington et al., Cyclopentyl Ethers and Their Preparation and Pharmaceutical Formulation, filed 9-14-87, U.S. Ser. No. 096,777.
Collington et al., Cyclopentyl Ethers and Their Preparation and Pharmaceutical Formulation, filed 9-11-87, U.S. Ser. No. 097,334.
Robert, *Gastroenterology* 77:761-7 (1979).

*Primary Examiner*—Ronald W. Griffin
*Attorney, Agent, or Firm*—Bernard, Rothwell & Brown

[57] ABSTRACT

The use is described of both (i) a systemic non-steroidal anti-inflammatory drug and (ii) a compound of formula (1)

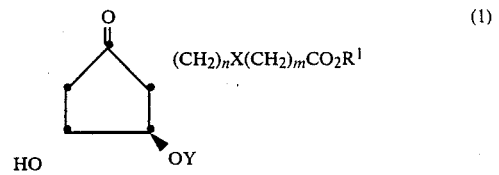

wherein
n is 1 or 2;
m is 2-5 and X is cis or trans —CH=CH— or —CH$_2$—CH$_2$—; or m is 1-4 and X is —CH=C=CH—;
R$^1$ is phenyl, substituted phenyl or naphthyl;
Y is substituted or unsubstituted 3-phenoxy-2-hydroxypropyl in the therapy or prophylaxis of inflammatory conditions and for analgesia in humans.

Pharmaceutical compositions containing both (i) and (ii) are also described.

25 Claims, No Drawings

ANTI-INFLAMMATORY COMPOSITIONS COMPRISING A SYSTEMIC NON-STEROIDAL ANTI-INFLAMMATORY DRUG AND A CYCLOPENTYL ETHER

This invention relates to improvements in the formulation of anti-inflammatory drugs for the treatment of inflammatory conditions and for analgesia.

Systemic non-steroidal anti-inflammatory drugs, such as aspirin, indomethacin and ibuprofen, are known to give rise to undesirable side effects. In particular, they are known to be ulcerogenic and can thus, for example, give rise to gastric and duodenal erosions and ulceration when administered orally. This side effect may be further enhanced in combination with other factors such as stress. Since in some treatments these compounds may have to be used for an extended period, such side effects can prove a serious disadvantage.

The present invention is based on our discovery that mucosal lesions of the gastrointestinal tract caused by non-steroidal anti-inflammatory drugs can be significantly reduced by co-administering a cyclopentyl ether described and claimed in GB-A-2174702 and set out in formula (1) below.

According to one aspect of the present invention, therefore, we provide a pharmaceutical composition which comprises a systemic non-steroidal anti-inflammatory drug and a compound of formula (1)

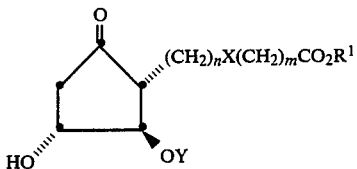

wherein
n is 1 or 2;
m is 2-5 and X is cis or trans —CH=CH— or —CH$_2$—CH$_2$—; or m is 1-4 and X is —CH=C=CH—;
$R^1$ is
(a) phenyl [optionally substituted by $C_{1-4}$ alkyl, $C_{1-4}$ alkoxy, $C_{1-4}$ alkanoyl, methylthio, methylsulphinyl, methylsulphonyl, halogen (e.g. chlorine or bromine), —CO$_2$R$^2$ [where R$^2$ is a hydrogen atom or $C_{1-4}$ alkyl or phenyl], —NHCOR$^2$ [where R$^2$ is as defined above or is a phenyl group optionally substituted by hydroxyl, CH$_3$CONH— or

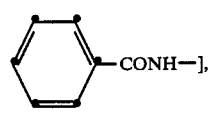

—CONR$^3$R$^4$ [where R$^3$ and R$^4$ may be the same or different and are each a hydrogen atom or $C_{1-4}$ alkyl group], —NHCONH$_2$, —CH$_2$CH(CONH$_2$)NHCOCH$_3$, or

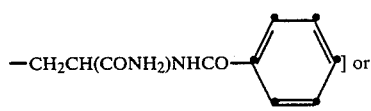

(b) 2-naphthyl;

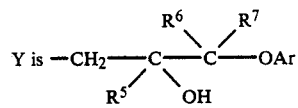

where $R^5$, $R^6$ and $R^7$ is each a hydrogen atom or a methyl group and at least one is a hydrogen atom; and Ar is a phenyl group (optionally substituted by one or two $C_{1-4}$ alkyl, $C_{1-4}$ alkoxy, $C_{1-4}$ alkylthio, $C_{1-4}$ alkylsulphinyl, $C_{1-4}$ alkylsulphonyl, halogen or trifluoromethyl groups); and the physiologically acceptable salts thereof.

The structural formula herein are to be understood to include the enantiomers of each of the compounds concerned as well as mixtures of the enantiomers including racemates.

In the definition of the compounds of formula (1) it is to be understood that the carbon atom carrying the chain —(CH$_2$)$_n$X(CH$_2$)$_m$CO$_2$R$^1$ is in the R-configuration.

The systemic non-steroidal anti-inflammatory drugs which may be employed in the compositions of the invention generally also show analgesic activity and include, for example, aspirin, indomethacin, ibuprofen, fenoprofen, ketoprofen, naproxen, mefenamic acid, diflunisal, benorylate, azapropazone, diclofenac, fenbufen, feprazone, fenclofenac, flufenamic acid, flurbiprofen, oxyphenbutazone, phenylbutazone, piroxicam, sulindac and tolmetin. They may be used in the pharmaceutical compositions of the invention in their usual dosage amounts, e.g. 50 mg-1 g of aspirin, 10-100 mg of indomethacin, 5-50 mg of piroxicam and 100-500 mg of ibuprofen per dosage regime for the drug in question. Particularly useful systemic non-steroidal anti-inflammatory drugs which may be employed in the compositions of the invention are indomethacin, piroxicam, ibuprofen and naproxen, especially indomethacin.

In general, the compounds of formula (1) in which the carbon atom carrying the group —(CH$_2$)$_n$X(CH$_2$)$_m$CO$_2$R$^1$ and/or the carbon atom in the group Y carrying the —OH group (particularly the former) are in the R-configuration and mixtures containing such isomers are preferred for use in the compositions of the invention.

The alkyl groups referred to above in the definition of the compounds of formula (1) may be straight or branched.

When $R^1$ in the compounds of formula (1) is phenyl substituted by a group —CO$_2$H the compounds are capable of salt formation with bases. Examples of suitable salts are alkali metal (e.g. sodium and potassium) salts.

Compounds of formula (1) in which the various substituents and groups have the meanings below are of particular use in all aspects of the invention.

In compounds where X is —CH=CH— or —CH$_2$CH$_2$—, m is preferably 3 when n is 1, and m is preferably 2 or 4 when n is 2. When X is —CH=C=CH—, m is preferably 2 and n is 1, and is 1 or 3 when n is 2.

When X is —CH=CH— it is preferably cis —CH=CH—.

When $R^1$ is a substituted phenyl group it may be, for example, phenyl substituted in the meta, ortho or, in particular, para positions by a chlorine or bromine atom or a methyl, ethyl propyl, n-butyl, t-butyl, methoxy, ethoxy, propoxy, butoxy, acetyl, propionyl, methylthio, methylsulphinyl, methylsulphonyl, —CO$_2$H, —CO$_2$CH$_3$, —CO$_2$CH$_2$CH$_3$, —CO$_2$— 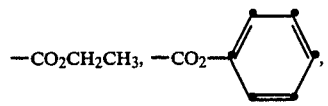, —NHCHO, —NHCOCH$_3$, benzoylamino, (acetylamino)benzoylamino, (hydroxy)benzoylamino, —CONH$_2$, —CONHCH$_3$ —CON(CH$_3$)$_2$, —CONHCH$_2$CH$_3$, —CON(CH$_2$CH$_3$)$_2$, —NHCONH$_2$, —CH$_2$CH-(CONH$_2$)NHCOCH$_3$ or —CH$_2$CH(CONH$_2$)NHCO— 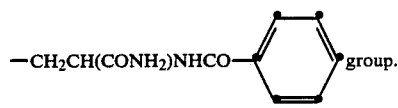 group.

Particularly useful substituents which may be present on a substituted phenyl group R$^1$ include C$_{1-4}$ alkoxy, C$_{1-4}$ alkanoyl, methylthio, methylsulphonyl, —CO$_2$R$^2$, —NHCOR$^2$, —CONR$^3$R$^4$ [where R$^2$, R$^3$ and R$^4$ are as defined for formula (1)], —NHCONH$_2$ or —CH$_2$CH-(CONH$_2$)NHCOCH$_3$ groups. Especially useful substituents of this type include methoxy, acetyl, methylthio, methylsulphonyl, —CO$_2$CH$_3$, —NHCOCH$_3$, benzoylamino, (p-acetylamino)benzoylamino, (p-hydroxy)-benzoylamino, —CONH$_2$, —CON(CH$_3$)$_2$, —NHCONH$_2$ or —CH$_2$CH(CONH$_2$)NHCOCH$_3$.

The group R$^1$ is preferably a substituted phenyl group where the substituent may be in the meta, ortho or, in particular, para positions, or is a 2-naphthyl group.

Compounds in which R$^1$ is a phenyl group substituted (particularly in the para-position) by a methoxy, acetyl, —CO$_2$CH$_3$, —NHCOCH$_3$, benzoylamino, —CONH$_2$, —CON(CH$_3$)$_2$ or —CH$_2$CH(CONH$_2$)NHCOCH$_3$ group, or R$^1$ is a 2-naphthyl group, are particularly useful.

In the group Y, R$^6$ and R$^7$ are preferably hydrogen atoms.

When the Ar phenyl group is substituted, the substituent may be in the meta, ortho or para positions and may be for example methyl, ethyl, propyl, butyl, methoxy, ethoxy, propoxy, butoxy, methylthio, methylsulphinyl, methylsulphonyl, fluoro, chloro, bromo or trifluoromethyl. Preferably, only a single substituent is present.

A preferred group of compounds of formula (1) for use in the compositions of the invention are those in which X is cis—CH=CH— and n is 1 and m is 3 or n is 2 and m is 2 or 4; R$^1$ is a phenyl group substituted (preferably in the para position) by a methoxy, acetyl, —CO$_2$CH$_3$, —NHCOCH$_3$, benzoylamino, —CONH$_2$, —CON(CH$_3$)$_2$ or —CH$_2$CH(CONH$_2$)NHCOCH$_3$ group or R$^1$ is 2-naphthyl; R$^5$ is a hydrogen atom or a methyl group; R$^6$ and R$^7$ are hydrogen atoms; and Ar is phenyl or phenyl substituted by fluoro or chloro. Compounds of this type in which the carbon atom carrying the —(CH$_2$)$_n$X(CH$_2$)$_m$CO$_2$R$^1$ group is in the R-configuration are particularly preferred. Especially preferred compounds of this type are those in which R$^1$ is a phenyl group substituted (preferably in the para position) by benzoylamino.

Preferred compounds of formula (1) for use in the compositions of the invention are:

[1R-[1α(Z),2β(R*),3α]]-(—)-4-Acetylphenyl 7-[3-hydroxy-2-(2-hydroxy-3-phenoxypropoxy)-5-oxocyclopentyl]-5-heptenoate;

[1R-[1α(Z),2β(R*),3α]]-(—)-4-(Acetylamino)phenyl 7-[3-hydroxy-2-(2-hydroxy-3-phenoxypropoxy)-5-oxocyclopentyl]-5-heptenoate;

[1R-[1α(Z),2β(R*),3α]]-(—)-4-(Benzoylamino)phenyl 7-[3-hydroxy-2-(2-hydroxy-3-phenoxypropoxy)-5-oxocyclopentyl]-5-heptenoate;

[1R-[1α(Z),2β(R*),3α]]-(—)-4-[4-(Acetylamino)benzoylamino]phenyl 7-[3-hydroxy-2-(2-hydroxy-3-phenoxypropoxy)-5-oxocyclopentyl]-5-heptenoate;

[1R-[1α(Z),2β(R*),3α]]-(—)-4-(Aminocarbonyl)phenyl 7-[3-hydroxy-2-(2-hydroxy-3-phenoxypropoxy)-5-oxocyclopentyl]-5-heptenoate;

[1R-[1α(Z,S*),2β(R*),3α]]-(+)-4-[2-(Acetylamino)-3-amino-3-oxo propyl]phenyl 7-[3-hydroxy-2-(2-hydroxy-3-phenoxypropoxy)-5-oxocyclopentyl]-5-heptenoate;

[1R-[1α(Z),2β(R*),3α]]-(—)-3-(Benzoylamino)phenyl 7-[3-hydroxy-2-(2-hydroxy-3-phenoxypropoxy)-5-oxocyclopentyl]-5-heptenoate;

[1R-[1α(Z),2β(R*),3α]]-(—) Methyl 4-[[7-[3-hydroxy-2-(2-hydroxy-3-phenoxypropoxy)-5-oxocyclopentyl]-1-oxo-5-heptenyl]oxy]benzoate;

[1R-[1α(Z),2β(R*),3α]]-(—)-4-[4-(Hydroxy)benzoylamino]phenyl 7-[3-hydroxy-2-(2-hydroxy-3-phenoxypropoxy)-5-oxocyclopentyl]-5-heptenoate

[1R-[1α(Z),2β(R*),3α]]-2-Naphthalenyl 7-[3-hydroxy-2-(2-hydroxy-3-phenoxypropoxy)-5-oxocyclopentyl]-5-heptenoate;

[1R-[1α(Z),2β,3α]]-4-(Methylsulphonyl)phenyl 7-[3-hydroxy-2-[2-hydroxy-3-[4-(methylthio)phenoxy]propoxy]-5-oxocyclopentyl]-5-heptenoate;

[1R-[1α(Z),2β(R*),3α]]-(—)-4-(Benzoylamino)phenyl 7-[3-hydroxy-2-(2-hydroxy-3-phenoxypropoxy)-5-oxocyclopentyl]-4-heptenoate;

[1R-[1α(Z),2β(R*),3α]]-(—)-4-(Benzoylamino)phenyl 9-[3-hydroxy-2-(2-hydroxy-3-phenoxypropoxy)-5-oxocyclopentyl]-7-nonenoate; and

[1R-[1α,2β(R*),3α]]-(—)-4-(Benzoylamino)phenyl 3-hydroxy-2-(2-hydroxy-3-phenoxypropoxy)-5-oxocyclopentaneheptanoate.

A particularly preferred compound for use in the compositions of the invention is the compound of formula (1) in which n is 1, m is 3, X is cis—CH=CH—, R$^1$ is 4-benzoylaminophenyl and Y is —CH$_2$CH(OH)CH$_2$O— 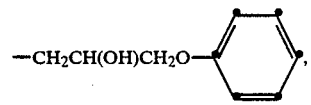, and in a particular aspect of the invention we thus provide a pharmaceutical composition which comprises a systemic non-steroidal anti-inflammatory drug and [1R-[1α(Z),2β(R*),3α]]-(—)-4-(benzoylamino)phenyl 7-[3-hydroxy-2-(2-hydroxy-3-phenoxypropoxy)-5-oxocyclopentyl]-5-heptenoate.

Another particularly preferred compound for use in the compositions of the invention is the compound of formula (1) in which n is 2, m is 2, X is cis—CH=CH—, R$^1$ is 4-benzoylaminophenyl and Y is

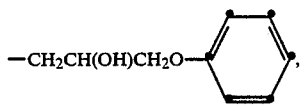

and in another particular aspect of the invention we thus provide a pharmaceutical composition which comprises a systemic non-steroidal anti-inflammatory drug and [1R-[1α(Z),2β(R*)3α]]-(−)-4-(benzoylamino)phenyl 7-[3-hydroxy-2-(2-hydroxy-3-phenoxypropoxy)-5-oxocyclopentyl]-4-heptenoate.

The amount of the compound of formula (1) employed in the compositions of the invention will be an amount sufficient to reduce the gastrointestinal distress caused by the anti-inflammatory drug and will preferably be in the range of 0.1 to 500 μg/kg body weight particularly 1 to 100 μg/kg body weight per dosage unit.

The precise dose administered of both the anti-inflammatory drug and the compound of formula (1) will of course depend on the age and condition of the patient and the frequency of administration (for example 1–4 times daily). The relative proportions of the anti-inflammatory drug and the compound of formula (1) employed in the composition of the invention will vary depending on the nature of the anti-inflammatory drug used but will in general be a simple ratio by weight of their usual dosage amounts as described above.

The pharmaceutical compositions of the invention may be used in the treatment of inflammatory conditions, particularly acute and chronic arthritides such as rheumatoid arthritis and osteo-arthritis, chronic musculo-skeletal inflammatory conditions such as ankylosing spondylitis and polymyalgia, acute and chronic injury and strain, and for analgesia in conditions such as dysmenorrhoea, especially where the use of the anti-inflammatory drug is limited by gastro-intestinal side effects.

According to a further aspect of the invention we provide the use of a composition containing as active ingredients a systemic non-steroidal anti-inflammatory drug and a compound of formula (1) in the therapy or prophylaxis of inflammatory conditions or for analgesia in human subjects.

In another aspect of the invention, we provide a method of treating inflammatory conditions or conditions such as dysmenorrhoea in human subjects which comprises administering to the patient effective amounts of a systemic non-steroidal anti-inflammatory drug and a compound of formula (1) in a single composition.

It will be appreciated that it is not necessary to administer the anti-inflammatory drug and the compound of formula (1) as a single composition in order to achieve an improvement in efficacy. Providing that both compounds are present at the same time in the subject to be treated the compounds may be administered separately, the compound of formula (1) preferably being administered first, followed by the anti-inflammatory drug.

In another aspect of the invention, therefore, we provide the use of a systemic non-steroidal anti-inflammatory drug and a compound of formula (1) in the presence of each other, for the therapy or prophylaxis of inflammatory conditions or for analgesia in human subjects.

In a further aspect of the invention we provide a method of treating inflammatory conditions or conditions such as dysmenorrhoea in human subjects which comprises administering to the patient effective amounts of a systemic non-steroidal anti-inflammatory drug and a compound of formula (1) in two separate compositions.

The ability of compounds of formula (1) to provide protection against the gastric and intestinal lesions produced by non-steroidal anti-inflammatory drugs, may be determined for example by their ability to inhibit indomethacin, peroxicam or aspirin induced gastric and intestinal lesions in the rat, following the methods of Whittle, (1976) Eur. J. Pharmacology 40 233 and Robert (1975) Gastroenterology 69 1045.

Compounds of formula (1) do not affect (a) the anti-inflammatory or (b) analgesic activity of non-steroidal anti-inflammatory drugs as determined for example by their ability not to affect (a) the anti-inflammatory activity of indomethacin in the carageenan-induced inflamed rat paw, following the method of Winter et. al. (1962) Proc. Soc. Exp. Biol. 111 544, or (b) the analgesic activity of indomethacin in the acetylcholine-induced writhing test in the mouse following the method of Tyers (1980) Br. J. Pharmacology 69, 503.

The compositions of the invention may be prepared by admixture of the active ingredients, and according to a further aspect of the present invention we provide a process for the preparation of a pharmaceutical composition comprising admixing a systemic non-steroidal anti-inflammatory drug and a compound of formula (1).

The compositions of the invention may be presented with the aid of at least one pharmaceutical carrier or excipient. Thus, in a further aspect of the invention we provide a pharmaceutical composition comprising as active ingredients a systemic non-steroidal anti-inflammatory drug and a compound of formula (1) together with one or more pharmceutical carriers or excipients.

In a still further aspect of the invention we provide a process for the preparation of a pharmaceutical composition which comprises admixing a systemic non-steroidal anti-inflammatory drug and a compound of formula (1) together with one or more pharmaceutical carriers or excipients.

Particularly useful compositions of the invention are those in a form suitable for oral, buccal or rectal administration.

The compositions may take the form of, for example, tablets, capsules, powders, solutions or syrups for oral administration. The compositions may thus contain as excipients, for example, binding agents, compression aids, fillers, lubricants, disintegrants and wetting agents. Tablets may be coated in a conventional manner, for example with a suitable film-forming material such as methyl cellulose or hydroxypropylmethyl cellulose. Alternatively the tablets may be sugar coated. Liquid preparations may also contain, for example, edible oils such as peanut, olive or sesame oils.

For buccal administration, the compounds may be formulated as tablets or lozenges in conventional manner; and for rectal administration compositions such as suppositories or retention enemas, for example containing conventional suppository bases such as cocoa butter or other glyceride, can be used.

The compositions of the invention may be prepared according to methods well known in the pharmaceutical industry. Thus, for example, tablets may be prepared by direct compression of the active ingredients blended with appropriate excipients. Alternatively, the blend of active ingredients and excipients may first be granulated using conventional techniques and the resulting granules compressed into tablets. Tablets may be film coated with suitable film forming materials using standard techniques.

Capsules may be prepared by blending the active ingredients and excipients and then filling the blend into gelatin capsules using a suitable filling machine.

According to a still further aspect of the present invention we provide a composition containing as active ingredients a systemic non-steroidal anti-inflammatory drug and a compound of formula (1) for use in the manufacture of a medicament for the therapy or prophylaxis of inflammatory conditions or for analgesia in human subjects.

It may be convenient to present the anti-inflammatory drug and the compound of formula (1) as a two container pack, one container containing the anti-inflammatory and the other containing the compound of formula (1). The compounds may then be admixed immediately before administration, or, if desired, may be administered sequentially.

The invention also provides a systemic non-steroidal anti-inflammatory drug and a compound of formula (1) and compositions containing them, in association with instructions for their use together in the therapy or propylaxis of inflammatory conditions or for analgesia in human subjects.

When a non-steroidal anti-inflammatory drug and a compound of formula (1) are administered in two separate compositions the composition containing a compound of formula (1) may be prepared according to the methods described in GB-A-2174702 and the composition containing a non-steroidal anti-inflammatory drug may be prepared according to conventional methods. The amount of each compound employed in the two compositions will preferably be in the ranges given above.

The following examples illustrate pharmaceutical compositions according to the invention. In the examples, the term "compound of formula (1)" may in particular be a compound [1R-[1α(Z),2β(R*),3α]]-(−)-4-(benzoylamino)phenyl 7-[3-hydroxy-2-(2-hydroxy-3-phenoxypropoxy)-5-oxocyclopentyl]-5-heptenoate or [1R-[1α(Z),2β(R*),3α]]-(−)-4-(benzoylamino)phenyl 7-[3-hydroxy-2-(2-hydroxy-3-phenoxypropoxy)-5-oxocyclopentyl]-4-heptenoate.

EXAMPLE A—TABLETS

These may be prepared by direct compression

|  | mg/tablet |
| --- | --- |
| Compound of formula (1) | 0.2 |
| Indomethacin | 50.0 |
| Magnesium stearate, BP | 2.0 |
| Microcrystalline cellulose, USP | 200.0 |
| to compression weight | |

The compound of formula (1) and the indomethacin are blended with about 10% of the microcrystalline cellulose then blended with the remaining microcrystalline cellulose and magnesium stearate. The blend is then compressed using 8 mm diameter punches into tablets on a suitable machine.

The tablets may be film coated with suitable film forming materials e.g. methyl cellulose or hydroxypropyl methylcellulose using standard techniques.

EXAMPLE B—CAPSULES

|  | mg/tablet |
| --- | --- |
| Compound of formula (1) | 0.2 |
| Indomethacin | 50.0 |
| Magnesium stearate, BP | 1.0 |
| * Starch 1500 | 200.0 |
| to fill weight. | |

* A form of directly compressible starch.

The compound of formula (1) and the indomethacin ae preblended with some of the Starch 1500 then this preblend is mixed with the remaining Starch 1500 and magnesium stearate. The mix is then filled into size No. 2 hard gelatin capsule shells using suitable machinery.

Tablets and capsules using other systemic non-steroidal anti-inflammatory drugs as described herein may be prepared in similar fashion to that above. It will however be appreciated that the dosage amounts may vary depending upon the systemic non-steroidal anti-inflammatory drug used.

We claim:

1. A method for the therapy or prophylaxis of inflammatory conditions or for inducing analgesia in the human body, which comprises administering thereto in the presence of each other therapeutically effective amounts of (i) a systemic non-steroidal anti-inflammatory drug and (ii) a compound of formula (1)

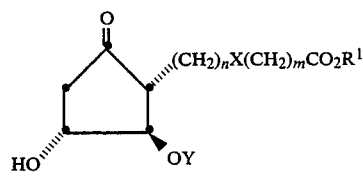

wherein
n is 1 or 2;
m is 2–5 and X is cis or trans—CH=CH— or —CH$_2$—CH$_2$—; or m is 1–4 and X is —CH=C=CH—;
R$^1$ is selected from the group consisting of phenyl, phenyl which has been substituted by a substituent selected from the group consisting of C$_{1-4}$ alkyl, C$_{1-4}$ alkoxy, C$_{1-4}$ alkanoyl, methylthio, methylsulphinyl, methylsulphonyl, halogen, —CO$_2$R$^2$ (where R$^2$ is a hydrogen atom or C$_{1-4}$ alkyl or phenyl), —NHCOR$^2$ (where R$^2$ is selected from the group consisting of a hydrogen atom or C$_{1-4}$ alkyl or phenyl, or a phenyl group substituted by a substituent selected from the group consisting of hydroxyl, CH$_3$CONH— or

—CONR$^3$R$^4$ (where R$^3$ and R$^4$ may be the same or different and are each a hydrogen atom or C$_{1-4}$ alkyl group), —NHCONH$_2$, —CH$_2$CH(CONH$_2$)NHCOCH$_3$, or —CH₂CH(CONH₂)NHCO 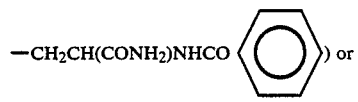 or 2-naphthyl;

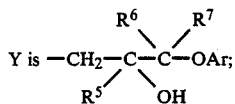

where $R^5$, $R^6$ and $R^7$ is each a hydrogen atom or a methyl group and at least one is a hydrogen atom; and Ar is selected from the group consisting of a phenyl group, a substituted phenyl group wherein said substituents are selected from the group consisting of one or two $C_{1-4}$ alkyl, $C_{1-4}$ alkoxy, $C_{1-4}$ alkylthio, $C_{1-4}$ alkylsulphinyl, $C_{1-4}$ alkylsulphonyl, halogen or trifluoromethyl groups, or a physiologically acceptacle salt thereof.

2. A method according to claim 1 in which the compounds (i) and (ii) are presented as separate compositions for said use.

3. A method according to claim 1 in which (i) is aspirin, indomethacin, ibuprofen, fenoprofen, ketoprofen, naproxen, mefenamic acid, diflunisal, benorylate, azapropazone, diclofenac, fenbufen, feprazone, fenclofenac, flufenamic acid, flurbiprofen, oxyphenbutazone, phenylbutazone, piroxicam, sulindac or tolmetin.

4. A method according to claim 1 in which (i) is indomethacin, piroxicam, ibuprofen or naproxen.

5. A method according to claim 1 in which (ii) is a compound of formula (I) in which:
X is cis—CH═CH— and n is 1 and m is 3 or n is 2 and m is 2 or 4;
$R^1$ is a phenyl group substituted by a methoxy, acetyl, —CO₂CH₃, —NHCOCH₃, benzoylamino, —CONH₂, —CON(CH₃)₂ or —CH₂CH(CONH₂)NHCOCH₃ group or $R^1$ is a 2-naphthyl group;
$R^5$ is a hydrogen atom or a methyl group;
$R^6$ and $R^7$ are hydrogen atoms; and
Ar is a phenyl or phenyl substituted by fluoro or chloro.

6. A method according to claim 1 in which in (ii) the carbon atom carrying the group —(CH₂)ₙX(CH₂)ₘCO₂R¹ is in the R-configuration.

7. A method according to claim 1 in which (ii) is [1R-[1α(Z̄),2β(R̄*),3α]]-(—)-4-(benzoylamino)phenyl 7-[3-hydroxy-2-(2-hydroxy-3-phenoxypropoxy)-5-oxocyclopentyl]-5-heptenoate.

8. A method according to claim 1 in which (ii) is [1R-[1α(Z̄),2β(R̄*),3α]]-(—)-4-(benzoylamino)phenyl 7-[3-hydroxy-2-(2-hydroxy-3-phenoxypropoxy)-5-oxocyclopentyl]-4-heptenoate.

9. A method according to claim 1 in which compounds (i) and (ii) are in a form suitable for oral, buccal or rectal administration.

10. A two-container pack for use in the therapy or prophylaxis of inflammatory conditions or for analgesia in humans, one of the containers containing (i) and the other containing (ii) as defined in claim 1.

11. A method according to claim 1 in which (i) is piroxicam and in which (ii) is [1R̄-[1α(Z̄),2β(R̄*),3α]]-(—)-4-(benzoylamino)phenyl 7-[3-hydroxy-2-(2-hydroxy-3-phenoxypropoxy)-5-oxocyclopentyl]-5-heptenoate.

12. A method according to claim 1 in which (i) is piroxicam and in which (ii) is [1R-1α(Z̄),2β(R̄*),3α]]-(—)-4-(benzoylamino)phenyl 7-[3-hydroxy-2-(2-hydroxy-3-phenoxypropoxy)-5-oxocyclopentyl]-4-heptenoate.

13. A pharmaceutical composition which comprises both a compound (i) and a compound (ii) as defined in claim 1.

14. A method for the therapy or prophylaxis of inflammatory conditions or for inducing analgesia in the human body, which comprises administering thereto in the presence of each other therapeutically effective amounts of (i) a systemic non-steroidal anti-inflammatory drug and (ii) a compound of formula

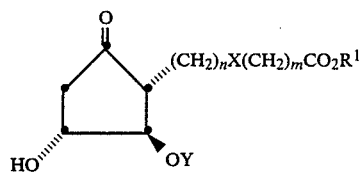

Wherein
X is cis—CH═CH— and n is 1 and m is 3 or n is 2 and m is 2 or 4;
$R^1$ is a phenyl group substituted by a methoxy, acetyl, —CO₂CH₃, —NHCOCH₃, benzoylamino, —CONH₂, —CON(CH₃)₂ or —CH₂CH(CONH₂)NHCOCH₃ group or $R^1$ is a 2-naphthyl group;

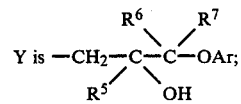

$R^5$ is a hydrogen atom or a methyl group;
$R^6$ and $R^7$ are hydrogen atoms; and
Ar is phenyl or phenyl substituted by fluoro or chloro.

15. A method according to claim 14 in which the compounds (i) and (ii) are presented as separate compositions for said use.

16. A method according to claim 14 in which (i) is aspirin, indomethacin, ibuprofen, fenoprofen, ketoprofen, naproxen, mefenamic acid, diflunisal, benorylate, azapropazone, diclofenac, fenbufen, feprazone, fenclofenac, flufenamic acid, flurbiprofen, oxyphenbutazone, phenylbutazone, piroxicam, sulindac or tolmetin.

17. A method according to claim 14 in which (i) is indomethacin, piroxicam, ibuprofen or naproxen.

18. A method according to claim 14 in which in (ii) the carbon atom carrying the group —(CH₂)ₙX(CH₂)ₘCO₂R¹ is in the R-configuration.

19. A method according to claim 14 in which (ii) is [1R-[1α(Z̄),2β(R̄*),3α]]-(—)-4-(benzoylamino)phenyl 7-[3-hydroxy-2-(2-hydroxy-3-phenoxypropoxy)-5-oxocyclopentyl]-5-heptenoate.

20. A method according to claim 14 in which (ii) is [1R-[1α(Z̄),2β(R̄*),3α]]-(—)-4-(benzoylamino)phenyl 7-[3-hydroxy-2-(2-hydroxy-3-phenoxypropoxy)-5-oxocyclopentyl]-4-heptenoate.

21. A method according to claim 14 in which compounds (i) and (ii) are in a form suitable for oral, buccal or rectal administration.

22. A two-container pack for use in the therapy or prophylaxis of inflammatory conditions or for analgesia in humans, one of the containers containing (i) and the other containing (ii) as defined in claim 14.

23. A method according to claim 14 in which (i) is piroxicam and in which (ii) is [1R-[1α(Z),2β(R*),3α]]-(—)-4-(benzoylamino)phenyl 7-[3-hydroxy-2(2-hydroxy-3-phenoxypropoxy)-5-oxocyclopentyl]-5-heptenoate.

24. A method according to claim 14 in which (i) is piroxicam and in which (ii) is [1R-1α(Z),2β(R*),3α]]-(—)-4-(benzoylamino)phenyl 7-[3-hydroxy-2-(2-hydroxy-3-phenoxypropoxy)-5-oxocyclopentyl]-4-heptenoate.

25. A pharmaceutical composition which comprises both a compound (i) and a compound (ii) as defined in claim 14.

* * * * *